(12) United States Patent
Tung et al.

(10) Patent No.: US 8,026,093 B2
(45) Date of Patent: Sep. 27, 2011

(54) PARTICULATE SUBSTRATES FOR IMPROVED RECOVERY OF MICROBES

(75) Inventors: Rosalind Tung, Piedmont, CA (US); George W. Chang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 521 days.

(21) Appl. No.: 12/267,824

(22) Filed: Nov. 10, 2008

(65) Prior Publication Data
US 2010/0120026 A1    May 13, 2010

(51) Int. Cl.
*C12N 1/00* (2006.01)
*C12N 1/12* (2006.01)

(52) U.S. Cl. .................................. 435/243; 435/252.1

(58) Field of Classification Search .................. 435/243, 435/252.1
See application file for complete search history.

(56) References Cited

OTHER PUBLICATIONS

Boyaci et al. 2005; Amperometric determination of live *Escherichia coli* using antibody-coated paramagnetic beads. Anal Bioanal Chem 382:1234-1241.*
Invitrogen, Ltd 2006; Dynabeads EPEC/VTEC 0103 improved testing efficiency during *E. coli* outbreak on the web at rapidmicrobiology.com/news/2646h2/php.*

* cited by examiner

*Primary Examiner* — Karen Carlson
(74) *Attorney, Agent, or Firm* — Richard Aron Osman

(57) ABSTRACT

Specially modified microbial growth surfaces improve bacterial recovery or counts when testing for the presence or absence of microbial cells or performing microbial enumerations.

20 Claims, No Drawings

PARTICULATE SUBSTRATES FOR IMPROVED RECOVERY OF MICROBES

INTRODUCTION

The field of the invention is the use of particulate surfaces for improved recovery of microbes from aqueous samples.

*Escherichia coli* (*E. coli*) and other coliforms are gram-negative, facultatively anaerobic bacteria normally inhabiting the gastrointestinal tract. Since *E. coli* and other fecal coliforms are normally found in animal feces, their presence has been long recognized and used as an indicator of possible fecal contamination in water and food. Therefore, much effort has been expended in devising and improving methods for detection, identification and quantitation of these bacteria.

Water and food sampling and testing have long been problematic due to the difficulty in detecting injured, dormant or dilute concentrations of bacteria. The present invention provides a method for improving bacterial recoveries and detection of *E. coli*, as well as other indicator or pathogenic bacteria, such as *Enterococcus, Salmonella, Listeria monocytogenes, Staphylococcus aureus, Clostridium perfringens, Campylobacter, Vibrio parahaemolyticus* and Entero-pathogenic *Escherichia coli* from such dilute samples.

In particular, the invention provides particulate substrate surfaces adapted to improve microbial recoveries or counts when testing for the presence or absence of microbial cells or performing bacterial enumerations. The surfaces act as growth catalysts, wherein dormant, injured, single or groups of microbial cells interact with or attach to the surface which subsequently promotes or causes physiological cellular changes in the cells. The physiological changes that follow interaction with the substrate surfaces permit resuscitation of injured cells and improve recoveries, especially with dilute numbers of microbes.

Current test methods do not employ specially adapted microbial growth surfaces for resuscitating injured microbes or recovering very dilute numbers of microbes. Instead, microbial enumerations are routinely performed in smoothly-surfaced borosilicate glass or plastic tubes, vials, bottles or wells. These conventional growth surfaces do not promote the physiological cellular changes and increased recoveries achieved with our improvement. Furthermore, improving microbial recoveries is a well studied topic in the field of microbiology but previous efforts have been directed towards manipulating the nutritive components of media, eliminating injurious chemicals or compounds, and carefully regulating sample storage time and temperatures.

SUMMARY OF THE INVENTION

The invention provides methods, assays and kits for improved recovery of a target bacterium or reference strain from an aqueous or homogenized sample, the general method comprising the steps of: (a) in a vessel, forming a mixture of determined amounts of a bacterial growth nutrient, a sterile particulate substrate, and an aqueous or homogenized sample comprising a target or known reference bacterium, wherein the substrate is chemically and nutritively inert to the bacterium yet is predetermined to promote recovery of the bacterium in the mixture; (b) incubating the mixture in the vessel under conditions wherein but for the presence of the substrate, the bacterium is unable to utilize the nutrient and multiply sufficiently to effect a detectable change in the mixture; and (c) detecting a resultant change in the mixture, wherein the change is diagnostic of the bacterium utilizing the nutrient and multiplying sufficiently to effect the change in the mixture.

In particular embodiments, the particulate substrate is fixed to an interior surface of the vessel or consists of a roughened or etched interior surface which mimics the presence of particulate substrates; the particulate substrate comprises glass microbeads, diatomaceous earth, clay, sand, insoluble biopolymers, plastic microspheres, silicon carbide (carborundum), foam, etc.; the sample is a milk, homogenized food, blood, aqueous, water supply, waste-water, finished-water, raw-water, well-water, salt-water, etc. sample; the sample is a dilute sample; the substrate does not form stable suspension in said mixture; the mixture further comprises a bacterial indicator agent, and the change is mediated by the indicator agent; the mixture further comprises a chromogenic or fluorogenic bacterial indicator agent, and the change is a color or fluorescence change mediated by the indicator agent; the assay is gasometric, ratiometric, immunological, nucleic acid-based, or colorimetric fluorogenic; and/or the bacteria are either indicator bacteria or direct pathogens, such as a *E. coli* and other coliforms, *Salmonella*, other sulfide-producing bacteria, *Shigella, Pseudomonas, Enterococci*, and/or *Vibrio*.

DETAILED DESCRIPTION OF PREFERRED EMBODIMENTS OF THE INVENTION

The invention provides particulate microbial growth surfaces that improve bacterial recovery or counts when testing for the presence or absence of microbial cells or performing microbial enumerations, wherein interaction of the target microbe with the surfaces prompts physiological changes that promote cellular resuscitation and/or improved culturability and recovery.

The general method comprises the steps of: (a) in a vessel, forming a mixture of determined amounts of a bacterial growth nutrient, a sterile particulate substrate, and an aqueous sample comprising a target bacterium, wherein the substrate is chemically and nutritively inert to the bacterium yet is predetermined to promote recovery of the bacterium in the mixture; (b) incubating the mixture in the vessel under conditions wherein but for the presence of the substrate, the bacterium is unable to utilize the nutrient and multiply sufficiently to effect a detectable change in the mixture; and (c) detecting a resultant change in the mixture, wherein the change is diagnostic of the bacterium utilizing the nutrient and multiplying sufficiently to effect the change in the mixture.

The disclosed use of sterile, particulate substrates to improve bacterial resuscitation and recovery may be adapted to a wide variety of microbial detection assays, particularly colorimetric or fluorometric substrate utilization assays. In general, the assays of the prior method are supplemented by adding to the incubation mixture the disclosed sterile particulate substrate to promote resuscitation and detection of one or more target bacterium mixture. This improvement permits the evaluation of samples, particularly samples containing injured and/or dilute concentrations of bacteria such as chlorinated drinking water samples, wherein detection would not otherwise be achieved by the prior methods without our improvement.

The substrate should be sterile, particulate, insoluble in the relevant medium, and chemically and nutritively inert to the bacterium, yet promote recovery of the bacterium in the mixture. The particulate substrate is typically in micron size ranges; for example, we have found particles in the range of 1 to 100 micrometers to be particularly effective in our *E. coli* assays. To maximize recovery, particle number should be in excess of initial, viable target bacterial counts, such as 10 to $10^6$ to one. A high proportion of the number of particles to bacteria cells permits each bacterium to have multiple contact points with the particulate substrate surfaces. Numerous contact points provides increased stimulation of favorable cellular recovery and growth factors, such as stimulation of the production of adhesive proteins and a subsequent increased growth response which follows.

In particular embodiments, the particulate substrate is glass microbeads, diatomaceous earth, clay, sand, insoluble biopolymers (protein, carbohydrate, lipid), plastic microspheres, silicon carbide (carborundum), synthetic nanoparticulate materials (see, e.g. Ali et al., January 2008, "Patents on Nanoparticulate Drug Delivery Systems—A Review", in Recent Patents on Drug Delivery & Formulation, Vol 2, No. 1, p. 83-89; Bentham Science Publishers), etc. Substances which may be adapted to provide suitable functional surfaces also include powdered or finely divided materials including silica gel beads, glass beads, protein or glycosaminoglycan-coated beads.

The particulate substrate is typically presented as a media additive, which may sink, float or be suspended in the mixture, and which can be added during the manufacturing process. For example, the substrate may comprise microspheres mixed homogeneously with the media. Alternatively, the substrate may be fixed to an interior surface of the incubation container, tube or vessel, like sand paper. For example, the particulate surfaces may be presented on (e.g. affixed to, or integrated into) the bottom interior of an incubation vessel allowing for cell attachment and the subsequent favorable physiological changes that follow. Alternatively, a disk with the characteristic surface of the invention may be fitted to the bottom of the incubation vessel and placed in the container prior to incubation. Alternatively, the surface is adapted to function with, on or in membrane a filter, such as a cellulose filter coated with microspheres. In yet another embodiment, the invention may be an alteration of the surface of the incubation container itself. For example, a plastic sample vessel may be ground or etched to produce a roughened interior surface with crevices that mimic adjacent particles.

In particular embodiments, the sample is potentially contaminated milk, cooking oil, homogenized food, blood, aqueous, water supply, waste-water, finished-water, raw-water, well-water, or sea-water. The samples are dilute with respect to viable, target microbes, which are typically present at concentrations less than $10^3$/mL. For example, contaminated drinking water samples may contain a chlorine residual which eradicates most bacteria, but may leave 1-10 chlorine-injured *E. coli* or other coliform bacteria cells per 100-mL volume. The invention improves detection of these stressed indicator microbes, especially at these dilute concentrations. Additionally, bacterial enumerations for samples such as source and recreational waters, wastewaters and foods are typically based on the MPN (most probable number) technique, which can be enhanced by the invention. In one version of the MPN technique, increasingly higher serial dilutions of a sample are analyzed, which final dilutions are carried beyond the extinction point for the presence of the target or indicator microbes. Overall, a combination of positive and negative results (in the highest dilutions) allows a statistical calculation to be performed that determines the "most probable number of bacteria" per volume. Therefore, the accuracy of the MPN testing format relies on a test medium's efficiency in detecting dilute numbers or even single cells of the target microbe at the highest dilutions. The current invention enables detection of the target microbe further down in the dilution series, which produces more accurate MPN enumerations. In another MPN format, a sample is mixed with a detection medium and divided into separate vessels, tubes or wells. Based on the combination of positive and negative vessels, tubes or wells observed, an MPN count can be generated. With the current invention, detection of the target microbe is provided in a higher number of vessels, tubes or wells, resulting in more accurate counts.

Microbes targeted for resuscitation and detection are often pathogenic microbes and/or microbes indicative of contamination, termed "indicator" microbes particularly coliform bacterium, such as *E. coli*.

In particular embodiments, the mixture further comprises a bacterial indicator agent, and the change is mediated by the indicator agent; for example, the mixture may further comprise a chromogenic or fluorogenic bacterial indicator agent, and the change is a color or fluorescence change mediated by the indicator agent. Suitable assay formats include gasometric, ratiometric, immunological, nucleic acid-based, colorimetric or fluorometric assays.

In more particular embodiments, the method provides an improvement to prior detection assays such as liquid format coliform, *Salmonella, Enterococci* or other *E. coli* detection media. For example, when enumerating bacteria in drinking, wastewater, recreational or surface and source water samples, a higher MPN count is achieved, due to the enhancement effect of the invention to allow a culture medium to more effectively detect dilute and/or injured target microbes.

EXAMPLES

In one example of the invention, 100-400 mesh calcium silicate, calcium carbonate, silicon carbide or glass powder is blended into a powdered culture medium in the concentration of 1 to 20% of the total volume of growth/detection medium. Such particulate matter components are readily sourced from chemical suppliers such as Thermo Fisher Scientific, VWR, Spectrum Chemicals and Alfa Aesar. In this example, a 100-mL water sample is added to the substrate-containing medium, exposing the target bacteria to a multitude of substrate surfaces. After contact with the substrate, bacteria cells will initiate favorable surface reactions stimulating generation of growth factors and subsequent reproduction. After incubation at 35 degrees C. for 16 to 48 hours, a positive result will be seen with the invention in cases where dilute or injured bacteria would normally produce a negative result.

In another example, a water sample is mixed with the substrate-containing growth detection medium, but divided into discrete portions in wells or tubes, with or without dilutions, for reading in an MPN or other enumeration format. The invention is compatible with tube formats, such as are described in section 9221 of the Standard Methods for the Examination of Water and Wastewater, APHA, AWWA, WEF. Additional enumeration formats may include the Idexx Quanti-Tray, Simplate, Bio-Rad Microplates or CPI's Quanti-Tag. In the case of tray formats, a higher number of positive wells will be observed, for example 40 positive wells instead of 20 that might otherwise be observed without the invention. In the case where dilutions are used, positive results will be seen further down in the dilution series, where smaller amounts of the sample are present.

In another example, a sample or incubation container is manufactured with an etched or ground interior area to create a complex textured surface that provides crevices with numerous contact points for bacteria, with crevices at least 0.3 um in width that allow bacteria to enter and lodge within the crevices. The modified surface may be at the bottom of the container and provide crevices, grooves or depressions allowing bacteria to lodge with exposure to multiple surface contact points simultaneously. The vessel may be used for collection of an aqueous sample in addition to acting as the incubation container and may be made of plastic, glass or other materials.

Examples of plastic containers that may be modified as disclosed herein include glass, polypropylene, polyethylene, polystyrene, polymethylpentene, polycarbonate or polystyrene bottles, such as those made by Scientific Specialties, Nalgene, Idexx or Crystalgen Inc. Exemplary glass containers include those made of borosilicate glass, soda lime glass, alumo silicate glass, or fused silica. Other examples of containers include generic glass or plastic culture tubes and MPN trays, such as the Quanti-Tray, and other enumeration trays or vessels. A further example of a container that may be used with this invention is an incubation vessel coupled with an integrated spectrophotometer, fluorometer or other measuring and/or recording system.

In the case of bottle or tube containers, bacteria which would normally go undetected, will be able to grow and reproduce in the presence of the invention to generate a positive detectable colorimetric, fluorometric or chemical responses (such as the indole, methyl red, Vogues Proskauer, and citrate tests for *E. coli* and other Enterobacteriaceae). A presence absence test that would normally generate a negative test result in the presence of very dilute bacteria would turn positive in the presence of the invention, increasing the effective sensitivity of the assay. In the case of the Quanti-Tray or other enumeration devices or trays, bacterial counts (reported as MPN/100-mL) would be increased by as much as 200% or higher.

In a fourth example, the invention provides a means to rejuvenate and recover bacteria after a period of stasis. Bacteria strains are often stored as cultures in the freeze dried state, on agars, or in a frozen state. Rejuvenation of these bacteria can be problematic due to injury and an extended period of stasis, taking up to a week to revive, while some cultures are not viable at all. With the current invention, bacteria subjected to injury by storage means or a period of dormancy could be rejuvenated for use more rapidly than would be realized without the invention, usually within 24 hours. In this example, a freeze-dried bacterium standard strain could be revived from storage (at 4-7 degrees C.) by incubation at 35 degrees C. for 24 hours in nutrient broth including 10 percent by volume (before hydration) of the substrate particulate matter. After the 24-hour incubation period, luxurious growth of the control standard will be visualizable by the naked eye. Numerous ATCC registered and other bacteria standard strains are used to support both research and quality control testing. Improved and more reliable recovery of such bacterial strains would be possible with the new invention. Some examples of bacteria which may be rejuvenated and may benefit from the recovery process are *Escherichia coli, Klebsiella pneumoniae, Listeria monocytogenes, Staphylococcus aureus, Campylobacter jejuni, Salmonella enterica, Clostridium*, amongst others.

In another example, plastic or glass beads 0.5 to 1.0 mm in diameter are pre-dispensed into a sample vessel to a depth of 2-5 mm over the bottom surface of the sample vessel. Alternatively, the bottom surface of the container may be covered with glass wool or fibers (e.g. 2 to 20, preferably 8 um diameter), such as commercially available from Thermo Fisher Scientific, VWR and other laboratory consumables suppliers. Upon addition of the sample, multiple substrate particles are available for contact with the target bacteria that will initiate subsequent favorable growth reactions and reproduction. Dilute or injured bacteria cells will produce a faster and more luxurious growth response, for example bacterial turbidity will be seen at 16 to 18 hours instead of 48.

In another example, 100 um rough calcium carbonate or glass particles are affixed to a 1-2 cm diameter paper disc or membrane filter that is added to a sample vessel. In this example, the sensitivity of a conventional bacteriological detection medium will be increased as target bacteria interact with the substrate particle disc. For example, a series of 10 sample vessels containing 1-10 indicator organisms per vessel will all turn positive, whereas a proportion of the vessels would otherwise be negative without the invention.

In another example, a naturally occurring porous material such as sponge or cellulose fibers are added to a bacteriological detection medium in the amount of 5 to 20% of the total dry powdered medium. Sponges may be made of cellulose, polyurethane or other materials with effective pore sizes ranging from 10-50 um. Upon hydration of the medium with water and addition of a bacteria-containing sample, target bacteria will be exposed to a multitude of inert substrate surfaces to which the bacterial cells can adhere with subsequent accelerated growth reactions.

The foregoing examples and detailed description are offered by way of illustration and not by way of limitation. All publications cited in this specification, and all publications cited therein, are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for improved recovery of a target bacterium from a dilute aqueous sample, comprising the steps of:
   in a vessel, forming a mixture of determined amounts of a bacterial growth nutrient, a sterile particulate substrate, and an aqueous sample comprising a target bacterium at a concentration of less than $10^3$/mL, wherein the substrate is chemically and nutritively inert to the bacterium yet is determined to promote recovery of the bacterium in the mixture;
   incubating the mixture in the vessel under conditions wherein but for the presence of the substrate, the bacterium is unable to utilize the nutrient and multiply sufficiently to effect a detectable change in the mixture; and
   detecting a resultant change in the mixture, wherein the change is diagnostic of the bacterium utilizing the nutrient and multiplying sufficiently to recover the bacterium and to effect the change in the mixture.

2. The method of claim 1, wherein the particulate substrate is fixed to an interior surface of the vessel.

3. The method of claim 1, wherein the particulate substrate comprises glass microbeads, diatomaceous earth, clay, sand, insoluble biopolymers, plastic microspheres, silicon carbide, or foam.

4. The method of claim 1, wherein the sample is a milk, cooking oil, homogenized food, blood, water supply, wastewater, finished-water, raw-water, well-water, or salt-water sample.

5. The method of claim 1, wherein the substrate does not form a stable suspension in said mixture.

6. The method of claim 1, wherein the mixture further comprises a bacterial indicator agent, and the change is mediated by the indicator agent.

7. The method of claim 1, wherein the mixture further comprises a chromogenic bacterial indicator agent, and the change is a color change mediated by the indicator agent.

8. The method of claim 1, wherein the assay is gasometric, ratiometric, immunological, nucleic acid-based, or colorimetric.

9. The method of claim 1, wherein the bacterium is a coliform bacterium.

10. The method of claim 1, wherein the particulate substrate is in the range of 1 to 100 micrometers diameter, and is present in particle number in 10 to $10^6$ excess of initial, viable target bacterial count of the sample.

11. The method of claim 1, wherein the bacterium is injured, and the method resuscitates the bacterium, wherein the bacterium is recovered from frozen or freeze-dried storage or dormancy within 24 hours.

12. The method of claim 1 further comprising the step of comparing the resultant change with a result of a control assay for the target bacterium in the absence of the substrate, wherein the method provides improved recovery of the target bacterium compared with the control assay.

13. The method of claim 12 wherein the control assay is a prior detection assays such as liquid format coliform, *Salmonella, Enterococci* or other *E. coli* detection media, the method enumerates bacteria in drinking, wastewater, recreational or surface and source water samples, and a higher most probable number (MPN) count is achieved over the prior detection assays due to an improved ability of the method to effectively detect dilute or injured target microbes.

14. The method of claim 12 wherein the method and control assays provides an MPN based on serial dilutions, wherein the method provides detection in more of the dilutions than the control assay.

15. The method of claim 12, wherein the method detects the bacterium (positive result) and the control assay does not (negative result).

16. The method of claim 12, wherein the method reports bacterial counts 200% higher than the control, reported as MPN/100-mL.

17. The method of claim 1 further comprising the step of comparing the resultant change with a result of a control assay for a bacterial standard comprising the same forming, incubating and detecting steps to detect the standard, wherein the standard is recovered from freeze-dried storage (at 4-7 degrees C.) by incubation at 35 degrees C. for 24 hours in nutrient broth including 10 percent by volume (before hydration) of the particulate substrate.

18. A method for improved recovery of a target bacterium from a dilute aqueous sample, comprising the steps of:
in a vessel, forming a mixture of determined amounts of a bacterial growth nutrient, a sterile particulate substrate, and an aqueous sample comprising a target bacterium at a concentration of less than $10^3$/mL, wherein the substrate is chemically and nutritively inert to the bacterium yet is determined to promote recovery of the bacterium in the mixture;
incubating the mixture in the vessel under conditions wherein but for the presence of the substrate, the bacterium is unable to utilize the nutrient and multiply sufficiently to effect a detectable change in the mixture; and
detecting a resultant change in the mixture, wherein the change is diagnostic of the bacterium utilizing the nutrient and multiplying sufficiently to recover the bacterium and to effect the change in the mixture,
wherein the sample contains a chlorine residual which eradicates most bacteria, but leaves 1-10 chlorine-injured *E. coli* or other coliform bacteria cells per 100-mL sample volume.

19. The method of claim 18, wherein the particulate substrate comprises glass microbeads, diatomaceous earth, clay, sand, insoluble biopolymers, plastic microspheres, silicon carbide, or foam; the sample is a milk, cooking oil, homogenized food, blood, water supply, waste-water, finished-water, raw-water, well-water, or salt-water sample; and the particulate substrate is in the range of 1 to 100 micrometers diameter, and is present in particle number in 10 to $10^6$ excess of initial, viable target bacterial count of the sample.

20. The method of claim 19 further comprising the step of comparing the resultant change with a result of a control assay for a bacterial standard comprising the same forming, incubating and detecting steps to detect the standard, wherein the standard is recovered from freeze-dried storage (at 4-7 degrees C.) by incubation at 35 degrees C. for 24 hours in nutrient broth including 10 percent by volume (before hydration) of the particulate substrate.

* * * * *